United States Patent
Gbaguidi et al.

(10) Patent No.: US 9,134,228 B2
(45) Date of Patent: Sep. 15, 2015

(54) METHOD FOR DETERMINING A CONCENTRATION OF A POLYSORBATE SPECIES IN A MIXTURE

(71) Applicant: GlaxoSmithKline Biologicals S.A., Rixensart (BE)

(72) Inventors: Benedicte Gbaguidi, Rixensart (BE); Olivier C Germay, Rixensart (BE); Sonia Lardau, Rixensart (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 0 days.

(21) Appl. No.: 14/402,849

(22) PCT Filed: May 21, 2013

(86) PCT No.: PCT/IB2013/001590
§ 371 (c)(1),
(2) Date: Nov. 21, 2014

(87) PCT Pub. No.: WO2013/175312
PCT Pub. Date: Nov. 28, 2013

(65) Prior Publication Data
US 2015/0129766 A1 May 14, 2015

Related U.S. Application Data

(60) Provisional application No. 61/650,735, filed on May 23, 2012.

(51) Int. Cl.
*G01J 5/02* (2006.01)
*G01N 21/3577* (2014.01)
*G01N 21/55* (2014.01)
*G01J 3/28* (2006.01)
*G01N 21/35* (2014.01)

(52) U.S. Cl.
CPC ........... *G01N 21/3577* (2013.01); *G01N 21/55* (2013.01); *G01J 3/28* (2013.01); *G01N 2021/3595* (2013.01)

(58) Field of Classification Search
CPC ............... G01N 2021/3595; G01N 21/552
See application file for complete search history.

(56) References Cited

U.S. PATENT DOCUMENTS

| | | | | |
|---|---|---|---|---|
| 5,866,430 A | * | 2/1999 | Grow | 506/6 |
| 6,040,191 A | * | 3/2000 | Grow | 506/12 |
| 2005/0287675 A1 | | 12/2005 | Packard et al. | |
| 2010/0304406 A1 | * | 12/2010 | Guo et al. | 435/7.21 |

FOREIGN PATENT DOCUMENTS

EP    1 382 964 A1    1/2004

OTHER PUBLICATIONS

Wenger N D et al., "An Automated Homogeneous Method for Quantifying Polysorbate Using Flourescence Polarization", Analytical Biochemistry, Academic Press, Inc., vol. 337, No. 1, pp. 48-54, Dec. 9, 2004.

* cited by examiner

*Primary Examiner* — Kiho Kim
(74) *Attorney, Agent, or Firm* — Virginia G. Campen

(57) ABSTRACT

The present invention relates to a method of measuring polysorbates, such as polysorbate 80, using Attenuated Total Reflectance-Fourier Transform Infrared spectroscopy (ATR-FTIR).

20 Claims, 9 Drawing Sheets

A Zoom on the area of interest. 7B is area of TWEEN only (for diff concentrations). Shows Response is not as good

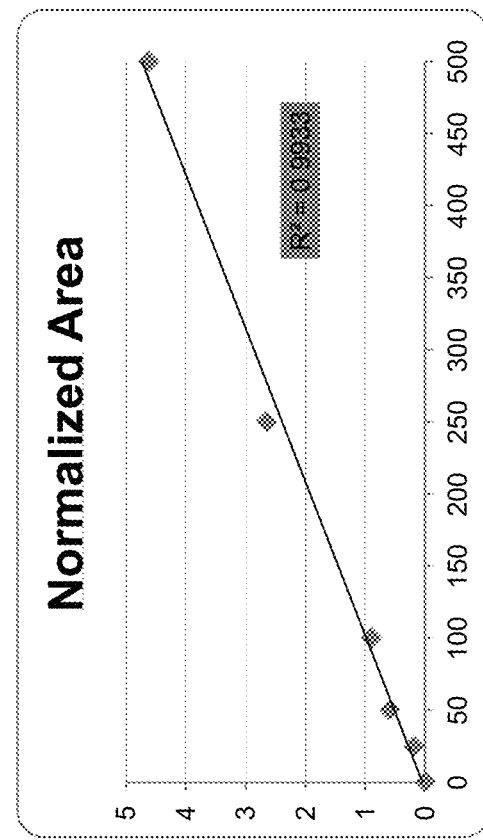
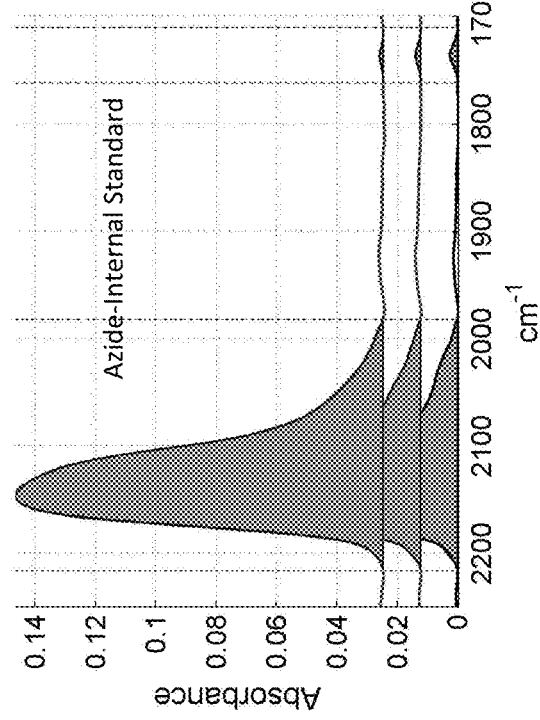
Figure 8A
Figure 8B

METHOD FOR DETERMINING A CONCENTRATION OF A POLYSORBATE SPECIES IN A MIXTURE

This application is filed pursuant to 35 U.S.C. §371 as a United States National Phase Application of International Patent Application Serial No. PCT/EP2013/001590 filed May 21, 2013, which claims priority to U.S. Patent Application No. 61/650,735 filed May 23, 2012 and the contents of each of the foregoing applications are hereby incorporated by reference.

STATEMENT REGARDING FEDERALLY SPONSORED RESEARCH

Aspects of this invention were made with United States government support pursuant to Contract #HHSO100200600011C, from the Department of Health and Human Services; the United States government may have certain rights in the invention.

TECHNICAL FIELD

The present invention relates to a method of measuring polysorbates, such as polysorbate 80, using Attenuated Total Reflectance-Fourier Transform Infrared spectroscopy (ATR-FTIR).

BACKGROUND

Techniques exist in the art for quantifying polysorbates, including methods based on colorimetry, HPLC separation, Gas Chromatography (GC), and GC with Mass Spectroscopy (MS) detection. However, interference may occur with such test methods due to constituents or conditions present within the test samples (matrix interference). This can necessitate specific, sometimes complex and time-consuming, preparation of the test sample.

SUMMARY OF THE INVENTION

One aspect of the invention is a method for determining the concentration of a polysorbate species in a mixture, by obtaining a test sample of the mixture, adding an internal standard to the test sample, obtaining a mid-infrared Attenuated Total Reflectance (ATR) spectra of the test sample, identifying from the reflectance spectra a wavenumber corresponding to the C=O peak and a wavenumber corresponding to the internal standard, calculating the area under the curve for the C=O wavenumber (normalized by the internal standard), and comparing said area to a calibration curve to determine the concentration of polysorbate in the test sample.

In one aspect of the invention the test sample comprises an antigen, such as a protein antigen or a polysaccharide antigen.

In one aspect of the invention, the test sample is not chemically pretreated prior to obtaining the mid-infrared attenuated total reflectance spectra of the test sample.

In one aspect of the invention, the internal standard is azide.

In one aspect of the invention, the test sample comprises a single polysorbate species.

In one aspect of the invention, the test sample is of a bulk vaccine component.

BRIEF DESCRIPTION OF THE DRAWINGS

FIG. 8A: depicts polysorbate 80 spectra using ATR-FTIR.

FIG. 8B: depicts quantification of polysorbate 80 using ATR-FTIR, where the peaks are normalized using azide as an internal standard.

DETAILED DESCRIPTION

Figure 1:
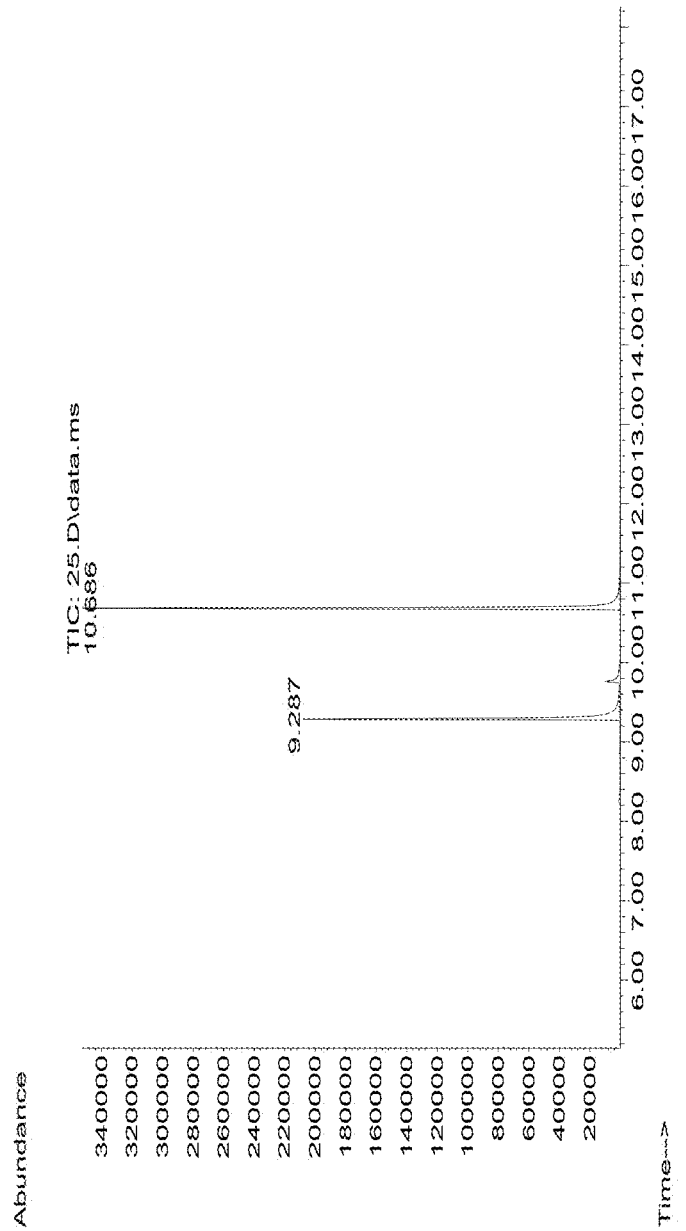
FIG. 1 is an example of a GC-MS chromatogram in Selected Ion Monitoring (SIM) mode (the peak labeled TIC: 25.D\data.ms 10.686 is Polysorbate 80).

Excipients are often added to pharmaceutical formulations, including vaccine formulations. Surfactants, including polysorbates, are commonly used excipients in pharmaceutical and vaccine preparations. Surfactants (such as polysorbates) can, for example, help retain the biological activity of proteins by maintaining a specific protein structure during storage, transportation and delivery. Surfactants may also help to decrease protein adsorption to surfaces (e.g., vials and syringes), reduce interfacial surface tension, and decrease the rate of protein denaturation (which can lead to protein aggregation). See, e.g., Khossravi et al., Pharma Research, 19(5): 634 (2002); Lougheed et al., Diabetes, Vol. 32 (1983) 424-432.

Polysorbate 20, polysorbate 40, polysorbate 60 and polysorbate 80 are common polysorbate excipients used in the formulation of biopharmaceuticals, including vaccines. The quantification of surfactants, as well as other ingredients, in medical, biopharmaceutical, and biological products may be required by regulatory agencies.

An Attenuated Total Reflectance-Fourier Transform Infrared spectroscopy (ATR-FTIR) method is disclosed herein that quantifies polysorbate in liquid formulations, including pharmaceutical formulations that comprise excipients other than polysorbate.

Methods of Quantifying Polysorbates

Various analytical methods have been described for quantification of polysorbates. Such methods may include multi-step sample preparation, potential interference within a complex matrix, and a lack of sensitivity and specificity.

Polysorbate 20 and/or 80 may be quantified based on the blue coloration of polysorbate species complexed with cobalt-thiocyanate reagent in an organic solvent; the concentration of polysorbate 20 and/or 80 is determined by optical absorption. Zsolt and Gabor, J. Pharmaceut. Biomed. Anal., 18 (1998) 715-720; Hu et al., J. Chromatogr. A, 984 (2003) 233-236; Adamo et al., J. Chromatogr. B, 878 (2010) 1865-1870; Tani et al., J. Chromatogr. A, 786 (1997) 99-106.

Fekete et al. describe an LC-CAD method for the quantitative determination of polysorbate 80, based on its interaction with 5(p-dimethylaminobenzylidene)rhodanine (PDR) in alkaline media (Fekete et al., J. Pharmaceut. Biomed. Anal., 52 (2010) 672-679). The method uses high performance liquid chromatographic (HPLC) separation and charged aerosol detection (CAD). Fekete et al. state that the LC-CAD method is suitable for quantifying Polysorbate 80 in the range of 10-60 μg/ml in protein solutions.

Size-exclusion high performance liquid chromatography (SEC-HPLC) with ultraviolet (UV) absorbance detection employs a mobile phase containing the surfactant to be determined at a concentration above its critical micellar concentration (CMC).

Reverse-Phase high performance liquid chromatography (RP-HPLC) with UV absorbance detection after sample preparation can be based on the acidic hydrolysis of the sorbitan laurate ester followed by a RP-HPLC separation with detection by UV absorbance of the free lauric acid (molar ratio 1:1). Zsolt et al., J. Pharmaceut. Biomed. Anal., 18 (1998) 715-720. Alternatively the basic hydrolysis of the sorbitan oleate ester can be used followed by RP-HPLC separation with detection by UV absorbance of the free oleic acid. Hu et al., J. Chromatogr. A, 984 (2003) 233-236; Adamo et al., J. Chromatogr. B, 878 (2010) 1865-1870; Tracy et al., AAPS J., 10 (51) (2008) 647.

Reverse-phase high performance liquid chromatography (RP-HPLC) with evaporative light scattering detection (ELSD) can achieve elution of polysorbate 80 as a single peak (co-elution of all polysorbate components). Nair et al., J. Chromatogr. A, 1012 (2003) 81-86; Hewitt et al., J. Chromatogr. A, 1215 (2008) 156-160; Adamo et al., J. Chromatogr. B, 878 (2010) 1865-1870; Hewitt et al., J. Chromatogr. A, 15:2138-45 (2011).

Gas chromatography (GC) with mass spectrometry (MS) detection uses the acidic hydrolysis of the sorbitan oleate ester followed by separation of the methyl ester oleate by GC with detection by mass spectrometry (MS). Sample preparation involves a hydrolysis procedure and then an extraction step. Polysorbate 80 is quantified against pentadecanoic acid as the internal standard (Oliveira et al., Talanta Vol. 69 (2006) 1278-1284).

Other analytical methods for quantification of polysorbates may include thin layer chromatography (TLC), supercritical fluid chromatography (SFC), fluorescence analysis with N-phenyl-1-naphtylamine fluorescent dyes partitioning into the hydrophobic core of micelles formed by polysorbate, quantitation of the polysorbate acid components by RP-HPLC after a derivatization reaction with 2-nitrophenylhydrazone, polysorbates characterization by using matrix assisted laser desorption/ionization time-of flight mass spectrometry (MALDI-TOF-MS), and liquid chromatography with mass spectrometry detection (MS).

IR Spectroscopy

Infrared (IR) vibrational spectroscopy identifies molecules by analyzing their chemical bonds, which vibrate at a characteristic frequency. Light radiation from 4000-400 $cm^{-1}$, the mid-infrared, is commonly used as the infrared region of the spectrum encompasses the fundamental frequencies of most molecular vibrations. In a molecule, the stretching and bending motions of a component (e.g. $CH_2$) results in multiple modes of oscillation. Oscillations that cause a change in dipole in the molecule result in absorption of a photon with the same frequency. A spectrum of the frequencies of absorption in a sample can be recorded and used to detect and quantify chemical groups present in the sample.

Attenuated Total Reflectance (ATR)

Attenuated Total Reflectance (ATR) is a sampling technique used with infrared spectroscopy. A test sample is placed in contact with an ATR crystal (alternatively referred to as an Internal Reflection Element (IRE)). Where liquid samples are tested, a shallow (thin) layer is spread over the ATR crystal. An incident beam of radiation (infrared light) is directed onto the ATR crystal at a pre-determined angle. The beam passes through the ATR crystal such that it is totally internally reflected at the boundary between the IRE and the test sample. The internal reflectance creates an evanescent wave extending only a few microns beyond the ATR crystal surface into the sample, and some of the energy of the incident radiation is absorbed by the test sample. The evanescent wave is thus attenuated or altered in regions of the infrared spectrum where the sample absorbs energy. The intensity of the internally reflected radiation is diminished for those wavelengths where the sample absorbs energy, and the amount of absorption at specific points can be used to quantify the amount of specific molecules in the test sample. The reflected radiation, therefore, includes information from which an absorption spectrum for the test sample can be acquired. The attenuated energy exits the ATR crystal, to a detector in the IR spectrometer. The system generates an infrared spectrum (internal reflection spectra or attenuated total reflection (ATR) spectra.

Because of the limited depth of penetration of the evanescent wave into the sample, test samples are placed in close contact with the ATR crystal; this can be achieved using liquid samples. The type of ATR crystal used defines its refractive index, the infrared transmission range, and the chemical properties of the IRE. The depth of penetration can be controlled by altering the angle of incidence of the incoming IR beam with respect to the IRE, or changing the refractive index of the ATR crystal.

Fourier Transform Infrared (FTIR) Spectroscopy

Fourier Transform Infrared (FTIR) Spectroscopy is based on the absorption of infrared light by molecules. Molecules only absorb infrared light at frequencies that affect the dipolar moment of the molecule; this causes excitation to higher vibrational states. Monatomic (He, Ne, etc.) and homopolar diatomic (H2, O2, etc.) molecules do not absorb infrared light.

FTIR spectroscopy obtains an infrared spectrum of absorption by a solid, liquid, or gas sample. A mathematical algorithm (Fourier transform) is used to convert raw data into a spectrum. In FTIR spectroscopy, a beam comprising different frequencies of light is directed at the sample, and measurements of absorption at different wavelengths are taken. All optical frequencies are observed simultaneously, over a period of time known as a scan time. The beam is changed (e.g., by using a Michelson interferometer, as is known in the art) to contain a different combination of frequencies and measurements are again taken. This is repeated to provide many data points (raw data) that are used to calculate the absorption at particular wavelengths.

Thus, in ATR-FTIR, changes that occur in an infrared beam at the boundary of the IRE and test sample are determined. When dealing with mid-IR spectra, the wavenumber (centimeter$^{-1}$) is commonly used rather than wavelength, because the wavenumber is proportional to the energy and frequency of the radiation.

The penetration depth of the infrared energy into the sample is wavelength dependent. As the wavelength of the infrared radiation increases, the depth of penetration increases. Stated alternatively, the depth of penetration increases as the wavenumber decreases. This causes the relative band intensities in the ATR spectrum to increase with decreasing wavenumber when compared to a transmission spectrum of the same sample. This phenomenon can be mathematically corrected via software, including commercially available FTIR software packages.

In ATR-FTIR the intensity signature of the returning incident spectrum, along with Beer's law, is used to identify and quantify compounds. Beer's Law underlies FTIR data analysis. It states that for a constant path length, the intensity of the incident (direct) light energy traversing an absorbing medium diminishes exponentially with concentration. Mathematical and statistical operations of the present method can be performed using any suitable computational equipment. The spectrometer may have the ability to store collected IR spectra (data) and perform mathematical manipulation of the data. A commercially available personal computer may be used to run software for the acquisition of data, the calculation of difference spectra, and the spectral and other analyses. Computers networked with an FTIR instrument can be employed to acquire data on one machine, while analyses are conducted on another. Suitable data acquisition and management software packages can be written de novo or can be purchased. Suitable commercially available software packages for use in the present invention include OPUS software (Bruker Optics, Germany); and Matlab (Mathworks Inc., USA) can be customized for use in this method. There are many suitable multivariate classification techniques for use with IR spectral data including, but not limited to, quantification methodologies such as partial least squares, principal component analysis (PCA) or principle component regression (PCR). A processed IR spectrum may be formed from several raw IR spectra (e.g., by multiple scans over a wavelength range and using averaging techniques known in the art).

Oliveira et al. describe assessment of ester content in biodiesel using FTIR based on the C=O stretching vibration of ester groups (Oliveira et al., Talanta Vol. 69 (2006) 1278-1284). U.S. Pat. No. 7,255,835 describes a single-pass method of ATR-FTIR for use in determining protein secondary structure.

Acquiring the IR Spectrum

The specific details for collecting and analyzing an IR spectra using ATR-FTIR vary with the specific equipment used, but generally comprise irradiating an IRE, which is in contact with a liquid test sample, with IR radiation and monitoring the radiation reflected from the IRE. Reflection data can be stored on a suitable medium and/or displayed on a computer screen or on chart paper.

A spectrum acquired using the apparatus and methods of the present invention may comprise a signal from the sample solvent; a background subtraction (mathematical subtraction) can be performed where the solvent is known. Biological components, such as proteins, glycoproteins, or polysaccharides, may be in solvents that comprise water or an aqueous buffer. An aqueous buffer may comprise compounds in addition to water. Phosphate buffered saline (PBS), tris (hydroxymethyl)aminomethane, HEPES (4-(2-hydroxyethyl)-1-piperazineethanesulfonic acid) and other compounds are commonly used to buffer solutions comprising biological molecules, such as polypeptide antigens. Subtraction of the buffer component can be achieved by mathematically subtracting the spectrum of the buffer (obtained in the absence of a sample) from the spectrum of the sample in the presence of buffer.

Background subtraction operations can also performed as needed to remove other background signals, such as from the clean ATR crystal.

Mathematically spectral subtraction operations can be performed on a computer system; the subtraction operation may comprise an algorithm that identifies (or allows a user to identify) regions of a composite spectrum for subtraction. After identifying regions to be subtracted, the subtraction is performed to generate a resultant difference spectrum. The difference spectrum may be presented graphically or tabulated as a function of absorbance at a given wavelength and presented in tabular form.

Present Method

The present method of quantifying polysorbate by ATR-FTIR is based on the detection and quantification of the carbonyl bond (C=O) of polysorbate. This bond is present in each of polysorbate 80, polysorbate 60, polysorbate 40 and polysorbate 20. Thus the present method is useful in the quantification of any of polysorbate 80, polysorbate 60, polysorbate 40 and polysorbate 20. In one embodiment, the sample contains only a single species of polysorbate (e.g., contains only polysorbate 80).

Even where the same amount of sample is placed on the ATR, the precise quantity of sample retained on the ATR element may vary, thus the present method uses a calibration curve created with an internal standard, to normalize for the quantity of sample retained on the ATR.

The present method allows determination of the concentration of polysorbate in a liquid test sample by ATR-FTIR spectroscopic technique without chemical pretreatment of the sample. The present inventors utilized a diamond IRE to obtain FTIR spectra of polysorbate 80. To create a calibration curve, and identify specific peaks of interest, the present inventors used a calibration set consisting of polysorbate 80 in $H_2O$, in concentrations of 20 µg/ml, 50 µg/ml, 100 µg/ml, 250 µg/ml, and 500 µg/ml. The peak area (C=O) of each spectrum at 1735 cm$^{-1}$, when normalized using an internal standard (azide), was found to be linearly correlated with the contents of polysorbate 80 ($R^2 > 0.99$). The results obtained from the ATR-FTIR method were confirmed by gas chromatography with mass spectrometry detection method (GC-MS).

The examples provided herein demonstrate an ATR-FTIR method for determination of polysorbate concentration in test samples of complex mixtures containing polypeptide components (examples provided herein utilized samples of purified bulk influenza virus produced in cell culture (Flu-CC)). It will be apparent to those skilled in the art that the sample used for quantification must be representative of the bulk from which it is obtained.

The present procedure for quantifying polysorbate in a formulation, including formulations that comprise antigen components, utilizes methods that will be apparent to those of skill in the art of spectroscopy upon consideration of the present disclosure. Equipment useful in the present method includes, but is not limited to, an ATR IRE, and FTIR spectrometer, and appropriate data processing equipment and software. The specific details of the procedure are governed by the parameters of the equipment and the nature of the experiment, but a general methodology is described herein. Additionally, the disclosed methodology can be adapted to the various properties of the sample under study and other pertinent experimental considerations.

One embodiment of the invention provides an ATR-FTIR method to quantify polysorbate in a sample. In one embodiment the sample comprises a polypeptide and/or a protein in a liquid (a liquid sample), such as polypeptides and/or proteins in water (an aqueous sample). In one embodiment the polypeptide is a polypeptide antigen.

One embodiment of the invention provides an ATR-FTIR method to quantify polysorbate in a sample, where the sample comprises a polysaccharide, such as a polysaccharide antigen. In one embodiment the sample comprises a polysaccharide in a liquid (a liquid sample), such as polysaccharides in water (an aqueous sample). In one embodiment the polysaccharide is a polysaccharide antigen.

In one embodiment the test sample is of a vaccine (including monovalent vaccine bulks as well as final vaccine formulations, including polyvalent vaccine formulations); in a further embodiment the test sample is of a vaccine that comprises an antigen from an organism selected from influenza virus, measles virus, mumps virus, varicella virus (chickenpox), rubella virus, herpes virus, polio virus, smallpox virus, poxvirus, Human Papillomavirus (HPV), Japanese encephalitis virus, hepatitis virus such as HepA or HepB, rotavirus, dengue virus, Respiratory Syncytial Virus (RSV), Cytomegalovirus (CMV), *Streptococcus pneumoniae, Neisseria meningitides, Corynebacterium diphtheriae, Clostridium tetani, Bordetella pertussis, Haemophilus influenzae, Salmonella typhi,* a *Streptococcus* species, a *Corynebacterium* species, a *Clostridium* species, a *Salmonella* species, and a *Bordetella* species.

In one embodiment, the sample is known to comprise a single polysorbate species selected from polysorbate 80, polysorbate 60, polysorbate 40, and polysorbate 20. Where a single polysorbate species is present in the sample, the results provide a measurement of the concentration of that polysorbate. The amount of sample must be sufficient to provide a thin layer of sample on the IRE.

In one embodiment of the present invention, the method employs a single pass ATR sampling technique and FTIR spectroscopy.

In one embodiment, the method comprises: (a) providing a sample comprising polysorbate and an internal standard; (b) providing an internal reflecting element (IRE); (c) contacting the sample with the IRE to form a sample-IRE interface; (d) using an FTIR device, or a device that contains focusing optics to permit the utilization of FTIR radiation, to direct a beam of infrared (IR) radiation through the IRE under conditions such that the IR radiation interacts with the sample-IRE interface; (e) recording the reflectance profile over the frequency range of 4000-600 $cm^{-1}$; (f) compiling the absorbance profile of the sample in a computer database, (g) generating an IR spectra of the sample in the frequency range of 4000-600 $cm^{-1}$, and (h) calculating the area (area under the curve) of the peak at 1735 $cm^{-1}$; determining the concentration of polysorbate in said sample by reference to a calibration curve.

In one embodiment, a calibration curve is established for each experiment or sample set tested. In one embodiment a single calibration curve is established and used for multiple samples, where the samples are from mixtures prepared by the same process. In one embodiment a calibration curve is established and used for multiple samples, where the samples are from mixtures prepared by the same process, for a set period of time.

Where only the presence of a polysorbate species (and not the quantity) is to be detected, a calibration curve is not required.

The specificity of the method for a particular matrix (e.g., a particular vaccine component) can be demonstrated using samples of the matrix spiked with known concentrations of polysorbate.

In one embodiment the internal standard is azide, and an IR spectra of the sample in the frequency range of 2200-1980 $cm^{-1}$ is generated.

In a further embodiment, the internal standard is azide, and an IR spectra of the sample comprising the frequency of 1735 $cm^{-1}$ is generated.

In one embodiment, the test sample is not pre-treated in a manner that alters the chemical structure of polysorbate ('chemical pre-treatment' or 'chemically pre-treated'), e.g., the polysorbate is not complexed with cobalt-thiocyanate, derivatized, transesterified, transbenzylated, treated to produce an ester derivative, and/or hydrolyzed. As used herein, addition of an internal standard that does not alter the chemical structure of the polysorbate is not considered 'chemical pre-treatment'.

In one embodiment, an internal standard is added to the test sample. In one embodiment, the internal standard is azide (linear anion that is isoelectric with $CO_2$).

In one embodiment, the present ATR-FTIR spectroscopy method for the quantification of polysorbate may be used for liquid formulations that contain (a) protein molecules, and/or (b) excipients in addition to a polysorbate (non-polysorbate excipients). In one embodiment, the present ATR-FTIR spectroscopy method for the quantification of polysorbate may be used for liquid formulations that contain (a) polysaccharide molecules, and/or (b) excipients in addition to a polysorbate (non-polysorbate excipients). Such non-polysorbate excipients include detergents other than polysorbate, for example, TRITON™ X-100 (4-(1,1,3,3-Tetramethylbutyl)phenyl-polyethylene glycol, t-Octylphenoxypolyethoxy ethanol, Polyethylene glycol tert-octylphenyl ether; available from Sigma Aldrich, St. Louis, Mo.) and Vitamin E succinate (VES).

In one embodiment of the present invention, the process of acquiring a spectrum of a sample is automated using suitable commercially available software packages for automated spectrum acquisition.

In another embodiment, the present invention is fully automated and can comprise an autosampler to inject and remove samples and a spectrum acquisition software package to run an FTIR spectrometer.

Terms

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Polysorbates are derived from PEG-ylated sorbitan (a derivative of sorbitol) esterified with fatty acids. Polysorbate species include polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate), and Polysorbate 80 (polyoxyethylene (20) sorbitan monooleate). The numeric designation following 'polysorbate' refers to the lipophilic group (monolaurate (20), monopalmitate (40), monostearate (60) and monooleate (80)). The number twenty (20) following 'polyoxyethylene' refers to the total number of oxyethylene groups in the molecule. Polysorbates are classified as non-ionic surfactants. Brand names for polysorbates include ALKEST™ and TWEEN™.

Polysorbate 80 is a non-ionic surfactant and emulsifier; brand names include Alkest TW 80, Canarcel and TWEEN™80. Polysorbate 20 is a non-ionic surfactant and emulsifier; brand names include Alkest TW 20 and TWEEN™20. Polysorbate 40 is a non-ionic surfactant and emulsifier; brand names include TWEEN™40. Polysorbate 60 is a non-ionic surfactant and emulsifier; brand names include TWEEN™60. The structures of polysorbate 80 and polysorbate 20 are shown below.

Polysorbate 80 (Sum of w, x, y and z is 20):

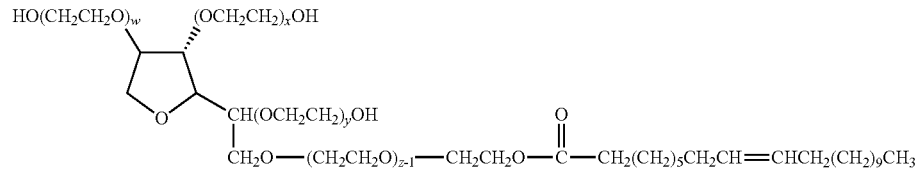

Polysorbate 20 (Sum of w, x, y and z is 20):

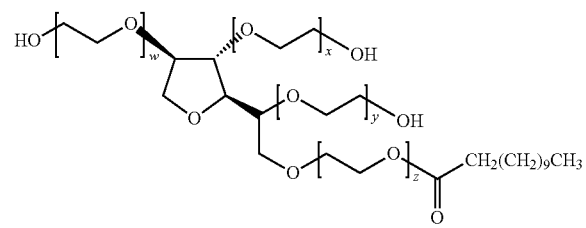

Polysorbates species, including polysorbate 80, polysorbate 60, polysorbate 40, polysorbate 20, and combinations thereof, are used as excipients in medical formulations, including vaccines, including vaccines to provide protection against influenza, Human Papillomavirus (HPV) infection, Japanese encephalitis, pneumococcal disease, hepatitis (HepB), and rotaviral disease; also combination vaccines such as DTaP (diphtheria, tetanus and acellular pertussis), DTaP/Hib (DTaP plus *Haemophilus influenzae* B). DTaP/IPV (DTaP plus inactivated poliovirus), and DTaP-HepB-IPV.

Influenza vaccines are prepared on various substrates. Many commercial vaccines are prepared using hen's eggs. More recently, influenza vaccines have been developed using cell lines such as Madin-Darby canine kidney (MDCK) cell line, MRC-5 cell line (human fetal lung), Vero cell line (African Green Monkey kidney epithelial cells), Chinese Hamster Ovary cell line (CHO), EB66® cell line, and PER.C6® cell line (human, Crucell (The Netherlands)). The EB66® cell line is a commercially available duck cell line derived from embryonic stem cells (Vivalis, Nantes, France) and used for the growth and production of vaccine components, including production of viruses used in the manufacture of viral vaccines, including influenza viruses. EB66® cells are susceptible to infection by many viruses, including avian influenza viruses. Alternative methods of vaccine component production include growth in embryonated chicken eggs and primary Chicken Embryo Fibroblasts (CEF).

As used herein, a formulation (or solution) containing (or comprising) a protein (or a polypeptide) component may be a medical composition, such as a biopharmaceutical composition, such as a therapeutic vaccine or a prophylactic vaccine, or a composition comprising an antibody, monoclonal antibody, or antigen-binding portion thereof.

As used herein, a formulation (or solution) containing (or comprising) a polysaccharide component may be a medical composition, such as a biopharmaceutical composition, such as a therapeutic vaccine or a prophylactic vaccine.

As used herein a vaccine may be one designed and intended for administration to a human or a non-human mammal. The vaccine may be prophylactic, to provide protection against a disease (reduce the chance of contracting the disease), or therapeutic (to treat a disease by lessening the symptoms, severity, duration, or risk of recurrence of the disease). The vaccine may be an anti-cancer vaccine. The vaccine may be monovalent or polyvalent.

As used herein a vaccine may comprise antigens obtained from a virus, including but not limited to: influenza virus, measles virus, herpes virus, polio virus, smallpox virus, poxvirus, Human Papillomavirus (HPV), Japanese encephalitis virus, hepatitis virus such as HepB, and rotavirus.

As used herein a vaccine may comprise antigens obtained from a bacterial species, including but not limited to: *Streptococcus pneumoniae, Corynebacterium diphtheriae, Clostridium tetani, Bordetella pertussis,* and *Haemophilus influenzae,*

As used herein, cGMP means current Good Manufacturing Practices.

As used herein, "bulk vaccine components" or "bulks" refer a vaccine active ingredient contained, or stored in, a volume larger than the volume of the finished vaccine. The concentration of vaccine active ingredient in a bulk is typically higher than the concentration of the active ingredient in the finished vaccine. A bulk is an intermediate product in the commercial manufacture of vaccines. A bulk may be univalent (monovalent), i.e., containing one purified antigen, bivalent, or multivalent. A bulk may contain the purified antigen in different concentrations than will be present in a final vaccine formulation (one for clinical use or commercial sale). In one embodiment the bulk contains at least one influenza virus protein antigen, for example, a neuraminidase (NA) or hemagglutinin (HA) antigen. The bulk may contain antigens derived from one strain of a pathogen, or from multiple strains of a pathogen. Final vaccine formulations may comprise multiple antigens (polyvalent vaccines), i.e., may be a mixture of multiple monovalent bulks, and may comprise antigens from multiple pathogens or multiple strains of a pathogen. Bulks may be stored until needed for the final preparation of vaccine doses. Vaccines may be in the form of a liquid, an adjuvanted liquid, or lyophilized.

As used herein, a sample is a representative portion of a larger volume. The sample may be of a mixture, such as a liquid comprising non-liquid elements. The sample may be an aqueous sample.

As used herein, a mixture comprises at least two different elements, e.g., a mixture comprising molecules of a polypeptide species and molecules of a polysorbate species. The mixture may be in solid form or liquid form.

As used herein, the terms "peptide", "polypeptide", and "protein" are interchangeable and mean a polymer of amino acids, regardless of size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" refer to both expressed gene products and chemically synthesized entities, and encompass glycoproteins and inactivated protein toxins (toxoids).

As used herein an antigen refers to a substance, including peptides and proteins (including glycoproteins), that induces an immune response in a mammal, including a human.

As used herein, quantification includes the determination of a concentration of a particular substance in a sample, e.g., in μg/ml, or the determination of the total amount of a substance in a particular volume.

As used herein, the term "aqueous" means comprising a water component. Thus an "aqueous solution" is a solution that comprises a water component. The terms "aqueous" and "aqueous solution" specifically encompass the inclusion of water, deuterium oxide or both as a water component.

As used herein, the term Internal Reflection Element (IRE) is used interchangeably with the term ATR crystal or ATR element, and means a crystal, prism or other structure that admits incoming radiation and reflects the radiation at least once from a surface (reflecting surface) on the interior of the element. In ATR-FTIR, reflectance follows interaction of the radiation with a sample in contact with the reflecting surface of the IRE. Following such a reflectance, the radiation can be re-reflected or emitted from the IRE. Many makes of spectrometers can be used with ATR, by adding an ATR device to the spectrometer. The FTIR spectrometer preferably has the capability to supply IR energy to a sample at a predetermined incident angle between about 30 to about 60 degrees, and collect reflected light from the sample through a broad range of angles including the incident angle.

IREs have a high refractive index (at least greater than that of the sample being tested, and typically between 238 and 4.01 at 2000 $cm^{-1}$), and may be an optically dense crystal, such as a germanium crystal, a zinc selenide crystal, a diamond crystal, or other high index of refraction material capable of transmitting IR light. The shape of an ATR crystal depends on the type of spectrometer and the sample it is used with, as is known in the art.

The angle of incidence, as used herein, is the angle at which incident light impinges on an IRE. In the present invention, a diamond ATR element can be used and a suitable angle of incidence is 45 degrees from surface normal.

As used herein, the term "multi-pass ATR" means an attenuated total reflectance technique in which radiation incident on an IRE having at least two reflection faces, interacts at least twice with a reflection face before exiting the IRE. Such interactions may be referred to as "bounces" or "passes". Multi-pass ATR generates a multi-pass ATR spectrum. As used herein, the term "single-pass ATR" means an attenuated total reflectance technique in which radiation incident on an IRE having at least one reflection face within the IRE interacts only once with a reflection face before exiting the IRE (one 'bounce' or 'pass'). Single-pass ATR generates a single-pass ATR spectrum.

As used herein, a calibration curve used in an embodiment of the invention, means a reference standard created using the same steps as recited in the method, but using samples (calibration samples) containing known amounts of a polysorbate species. The polysorbate species in the calibration sample is the same as in the test samples, and the amounts of the polysorbate species in the calibration sample span a range encompassing the range reasonably expected, by one skilled in the art, to be present in the test samples. For example, where the polysorbate concentration in the test samples is expected to range between zero and 500 μg/ml, calibration samples containing 0 μg/ml, 25 μg/ml, 50 μg/ml, 100 μg/ml, 250 μg/ml and 500 μg/ml may be used to prepare a calibration curve. Any suitable unit of area may be used for the calibration curve.

The singular terms "a," "an," and "the" include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance and stated to be "about" a certain level, are intended to be approximate. Thus, where a concentration is indicated to be "about 250 μg/ml" (for example), it is intended that the concentration be understood to be at least approximately (or "about" or "~") 250 μg/ml.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is used herein to indicate a non-limiting example and is synonymous with the term "for example."

To facilitate review of the various embodiments of this disclosure, the following explanations of terms are provided. Additional terms and explanations can be provided in the context of this disclosure.

A fast and sensitive method has been developed for the quantification of polysorbate in liquid formulations, including formulations comprising proteins (including glycoproteins) and/or polysaccharides. The method is also suitable for the quantification of polysorbate in liquid formulations containing other (non-polysorbate) excipients, and in liquid formulations containing both proteins and other (non-polysorbate) excipients.

EXAMPLES

Example 1

Method of Quantifying Polysorbate 80 by GC-MS

Gas Chromatography-Mass Spectrometry (GC-MS) is a commonly used and validated method for measuring the content of polysorbate 80 in liquid samples.

Samples and standards were treated using a two step procedure:
(1) Derivatization: methanol+HCl Fischer trans-esterification
(2) Extraction of derivatization product: Hexane/aqueous media partitioning Transmethylation of polysorbate 80 (using MeOH+HCl) provides 9-octadecenoic acid, methyl ester.

An internal standard (Pentadecanoic acid) was used to account for the variability of the derivatization step. Chromatographic separation was obtained using a fused silica capillary column (Varian WCOT (Wall Coated Open Tubular) Ulti-metal 25 m×0.25 mm column coated with TAP-CB DF=010 (Agilent Technologies, Santa Clara, US). Calibration range was 50 to 2000 μg/ml. Mass Spectrometry detection of Polysorbate 80 and Internal Standard (IS) was at specific m/z (mass-to-charge ratio).

Samples and standards were prepared by mixing:
200 μl of Sample or Standard
200 μl pentadecanoic acid (Internal standard, IS)
400 μl of MeOH/HCl 4N.

Samples (or standards) were then heated for one hour at 80° C., and 400 μl of hexane was added to extract the methyl ester derivative. Samples (or standards) were then centrifuged for five minutes at 11000 RPM. The hexane phase was collected and analyzed by GC-MS.

Table 1 shows the mass-to-charge ratio (m/z) used for GC-MS detection of the Internal Standard and Polysorbate 80, and the retention time of these components.

TABLE 1

| Analyte | m/z | Retention time |
| --- | --- | --- |
| Pentadecanoic acid (IS) | 256-143 | 9.29 min |
| Polysorbate 80 | 264-296 | 10.69 min |

FIG. 1 is an example of a GC-MS chromatogram in SIM mode showing the polysorbate 80 peak. The first peak corresponds to the internal standard (known quantity), and the second peak (labeled TIC:25.D\data.ms 10.686 (TIC=Total Ion Count)) corresponds to the derivatized polysorbate. The number of counts indicates abundance.

Example 2

ATR-FTIR Procedure

A method of quantifying polysorbate using ATR-FTIR was developed using samples obtained during the production of bulk inactivated influenza vaccine components.

Influenza virus was produced in EB66® cells. The viral harvest was separated from the cells and purified to produce a bulk concentrate using the following successive steps: centrifugation, microfiltration, ultrafiltration, sucrose gradient ultracentrifugation, β-propiolactone inactivation, ultraviolet (UV) light inactivation, ultrafiltration, split (disruption and inactivation of the whole virus), ultracentrifugation, chromatography, ultrafiltration, and filtration 0.22 μm.

Purified final bulks comprised influenza protein antigens and excipients.

ATR-FTIR spectra were recorded at room temperature on a TENSOR™ 27 FT-IR single beam spectrophotometer (Bruker Optics, Ettlingen, Germany) equipped with a liquid nitrogen-cooled mercury/cadmium/telluride detector at a nominal resolution of 4 $cm^{-1}$ and encoded every one $cm^{-1}$. The spectrophotometer was continuously purged with dried air. A background absorbance spectra was conducted before each sample (IRE without sample). This 'blank' was subtracted from the sample's measured spectrum by the software used.

Approximately 1 μL of sample was spread on the internal reflection element (IRE) and the solvent was slowly evaporated under a gentle nitrogen flow. The IRE was a diamond crystal (Golden Gate Reflectance ATR, Reflex Analytical Corporation, Ridgewood, N.J., USA; single reflection) transparent to the infrared (IR) radiation of interest. A standard sealed and purgeable optics housing was used; a Michelson interferometer was used.

For each sample, spectra were recorded from 4000 to 600 $cm^{-1}$ and for each sample multiple scans were averaged.

Spectrum region 3000-2800 $cm^{-1}$ is assigned to polysorbate 80 aliphatic chain; 2200-1980 $cm^{-1}$ peak corresponds to internal standard (azide); peak at 1735 $cm^{-1}$ is from polysorbate 80 (C=0 stretching); peak at 1100 $cm^{-1}$ is assigned to polysorbate 80 C-0 bond. (See Coates, The Interpretation of Infrared Spectra: Published Reference Sources, Applied Spectroscopy Review, Vol. 31 (1-2), 179-192 (1996); Smith, Infrared Spectral Interpretation, a Systematic Approach, CRC Press, Boca Raton, Fla., 1999.) Peak areas (I), (III) and (IV) were normalized using azide peak area (II) (internal standard).

As described in Examples 3 and 4, calibration curves were created using calibration samples containing known amounts of polysorbate, and specific peaks of interest were identified, using reference standards with known concentrations of polysorbate 80. Reference standards were (1) solutions of polysorbate 80 in $H_2O$ (20, 50, 100, 250 and 500 μg/ml), and (2) samples of purified bulk Flu-CC with known concentrations of polysorbate 80 added. The reference standards also contained azide as the internal standard (0.2% azide w/v; diluted ten time to provide final 0.02% of azide). Data analysis was performed using the OPUS software (Bruker Optics, Germany) and Matlab (Mathworks Inc., USA).

Figure 2:
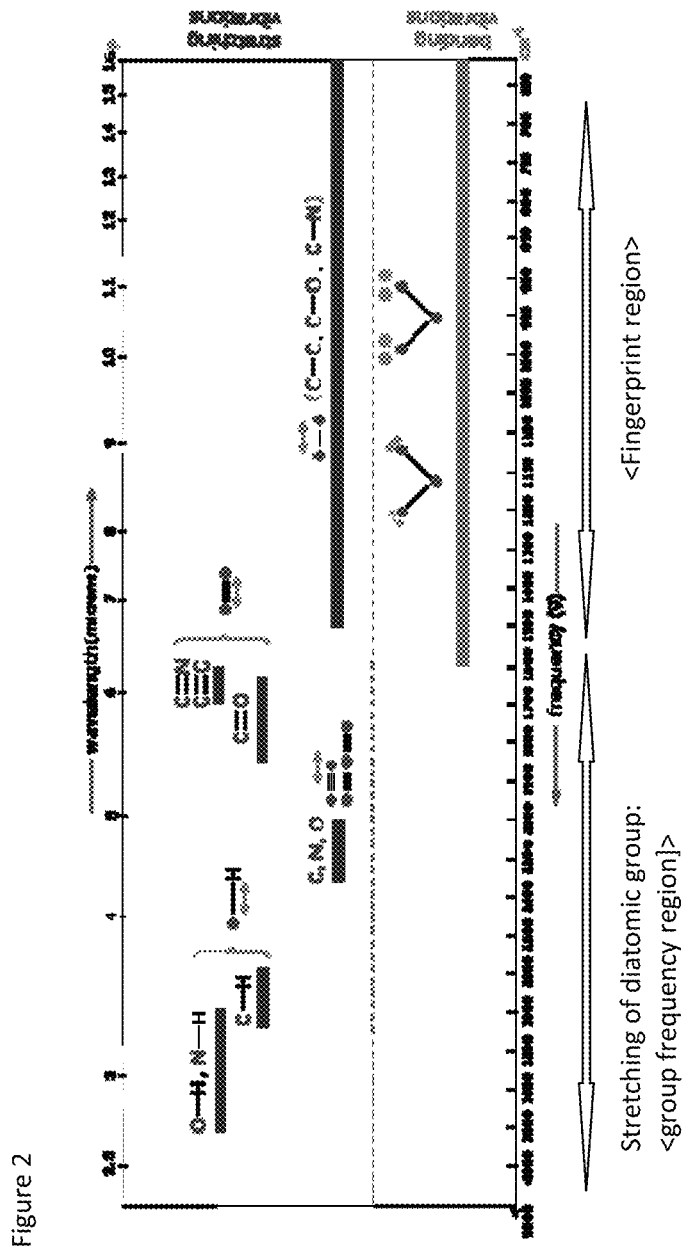
FIG. 2 depicts vibrational modes of chemical bonds. The location of the vibrational modes is given in terms of wavelength and frequency.

General vibrational modes are depicted in FIG. 2. Mid-infrared, approximately 4000-400 $cm^{-1}$ (1.4-3.0 μm), is used to study the fundamental vibrations and associated structure. For example, vibrational modes for a $CH_2$ group include symmetrical stretching ($v_s$ $CH_2$ approximately 2853 $cm^{-1}$), asymmetrical stretching ($v_{as}$ $CH_2$ approximately 2926 $cm^{-1}$), in-plane bending or scissoring (δs $CH_2$ approximately 1465 $cm^{-1}$), in-plane bending or rocking (ρ $CH_2$ approximately 720 $cm^{-1}$), out-of-plane bending or wagging (w $CH_2$ 1350-1150 $cm^{-1}$), out-of-plane bending or twisting (τ$CH_2$ 1350-1150 $cm^{-1}$).

Example 3

ATR-FTIR Detection of Polysorbate in Water

Using the method as described in Example 2, the concentration of polysorbate was investigated using 20 μg/ml, 50 μg/ml, 100 μg/ml, 250 μg/ml and 500 μg/ml of polysorbate 80 in water (single initial sample diluted to create the differing concentrations). Each sample contained azide (0.02% w/v) as an internal standard.

Figure 3:
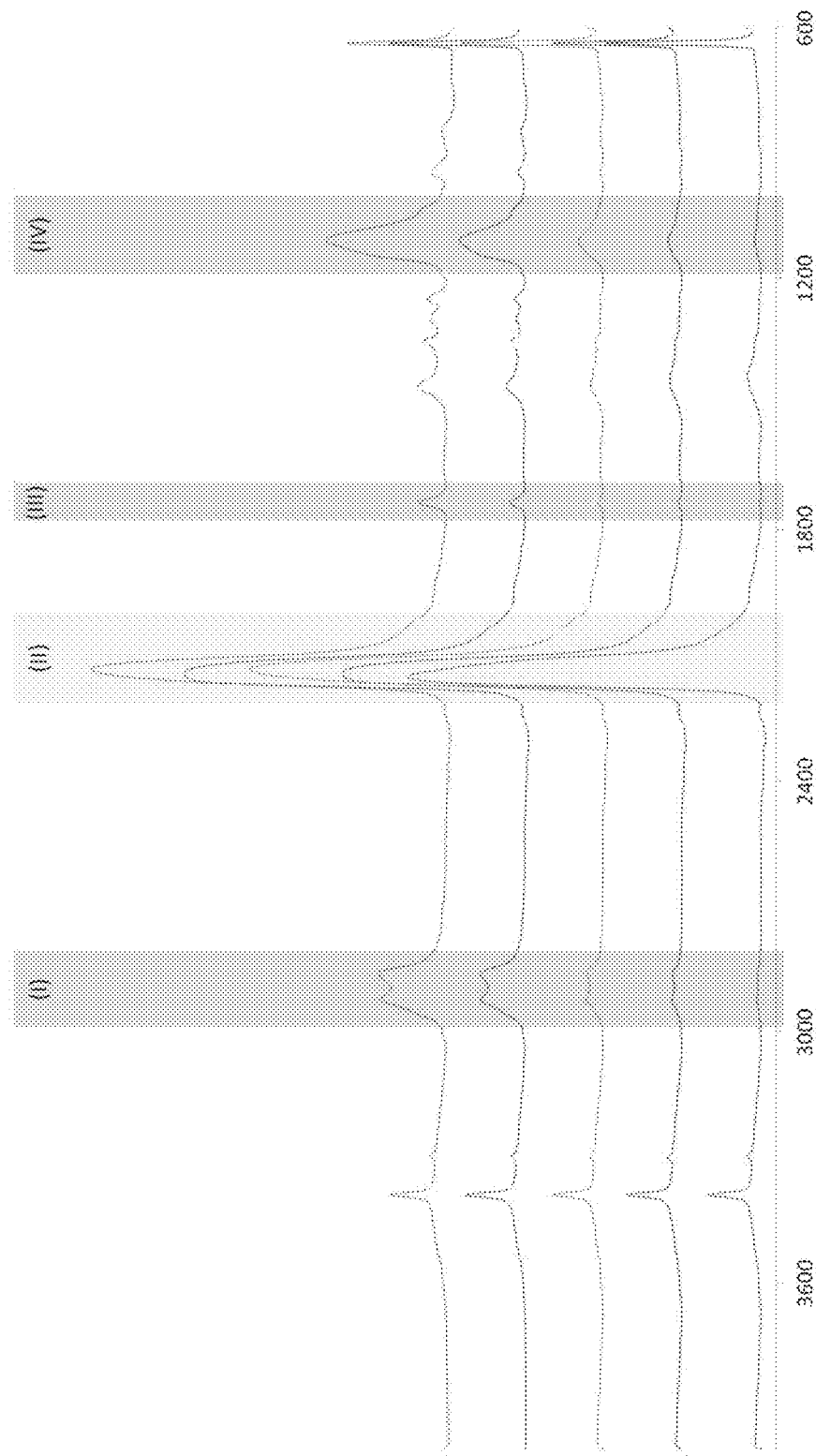
FIG. 3 shows an ATR-FTIR spectra obtained from known concentrations of polysorbate 80 in solution (water), normalized using the internal standard (region II), where the X axis is wavenumber ($cm^{-1}$) and the Y axis is absorbance (normalized absorbance in arbitrary units). Spectrum region (I) 3000-2800 $cm^{-1}$=polysorbate 80 aliphatic chain; region (II) 2200-1980 $cm^{-1}$=internal standard added to the sample; region (III) peak at 1735 $cm^{-1}$=polysorbate 80(C=O); region (IV) peak at 1100 $cm^{-1}$=polysorbate 80 (C-0). Peak areas (I), (III) and (IV) increase as a function of polysorbate 80 concentration. Each line on the graph represents an averaged result for a sample, from 32 scans.

FIG. 3 shows an example of spectra obtained from the polysorbate 80/water dilutions. Each line represents one of the samples (20 μg/ml, 50 μg/ml, 100 μg/ml, 250 μg/ml and 500 μg/ml of polysorbate 80 in water), and is an averaged value from 32 scans. (Averaged results of 256 scans per sample were also prepared (not shown), and gave the same correlation as the averaged results of 32 scans). Spectrum region 3000-2800 $cm^{-1}$ is assigned to polysorbate 80 aliphatic chain; 2200-1980 cm$^{-1}$ peak corresponds to internal standard (azide); peak at 1735 cm$^{-1}$ is from polysorbate 80 (C=O stretching); peak at 1100 cm$^{-1}$ is assigned to polysorbate 80 C-0 bond. (See Coates, The Interpretation of Infrared Spectra: Published Reference Sources, Applied Spectroscopy Review, Vol. 31 (1-2), 179-192 (1996); Smith, Infrared Spectral Interpretation, a Systematic Approach, *CRC Press*, Boca Raton, Fla., 1999.)

The five lines on FIG. 3 represent the five polysorbate/water dilution samples. Peak areas (I), (III) and (IV) are polysorbate normalized using the azide (internal standard, shown at peak area (II)).

Region (I) 3000-2800 cm$^{-1}$=polysorbate aliphatic chain;
Region (II) 2200-1980 cm$^{-1}$=internal standard, azide;
Region (III) peak at 1735 cm$^{-1}$=polysorbate (C=0);
Region (IV) peak at 1100 cm$^{-1}$=polysorbate (C-0).
Peak areas (I), (III) and (IV) were identified as increasing as a function of polysorbate 80 concentration.

Figure 4:
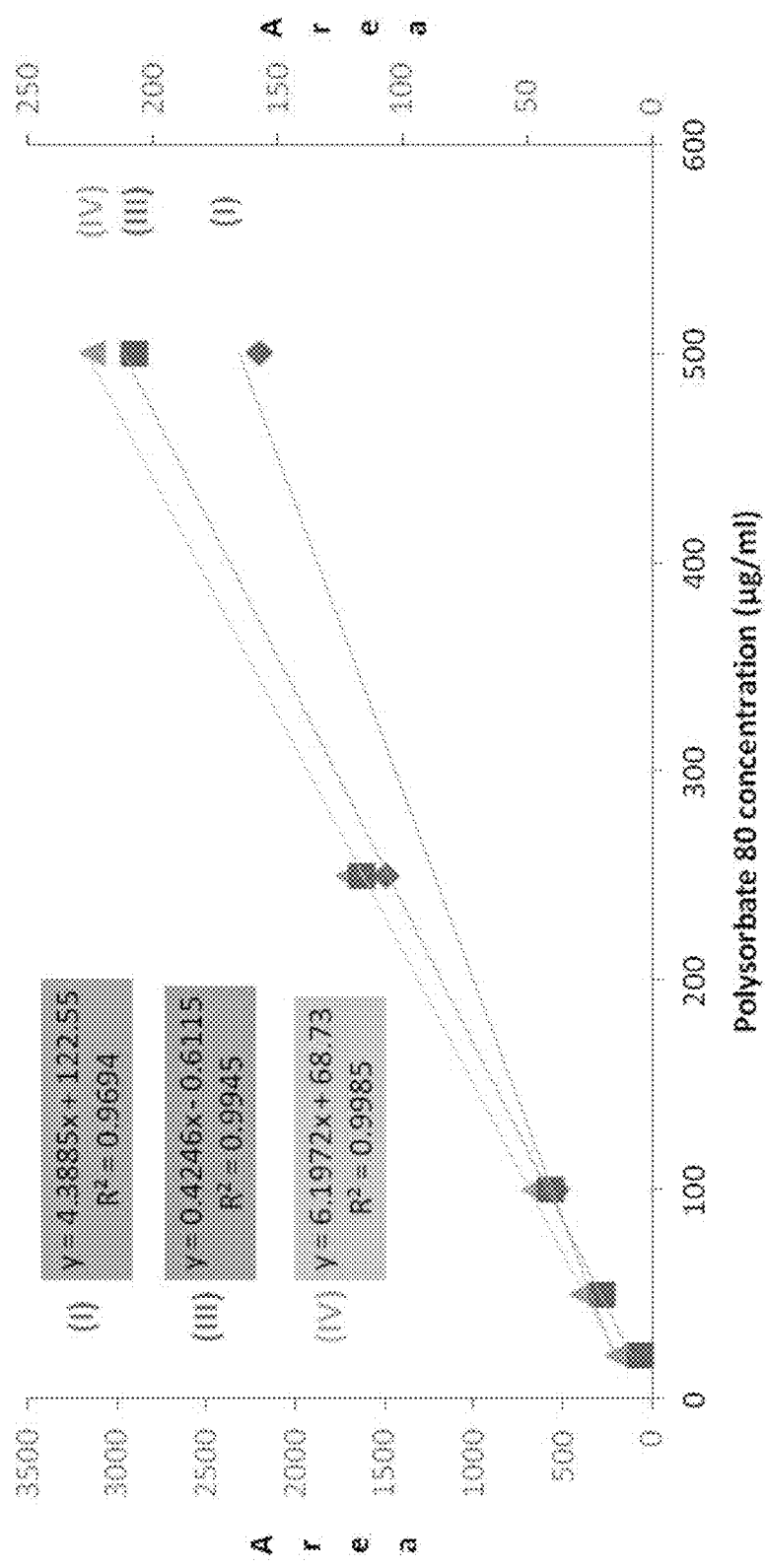
FIG. 4 shows calibration curves obtained from Regions (I), (III) and (IV) of FIG. 3, normalized using the azide standard Region II. The area (Y axis) is expressed as arbitrary units; the X axis is polysorbate 80 concentration (μg/ml).

From these five spectra the linear regression of FIG. 4 was plotted. FIG. 4 plots the proportions of peak areas (I, III and IV; normalized using the internal standard). The area is expressed as arbitrary units. The polysorbate 80 dose-response was shown to be linear in this range with coefficients of determination R$^2$ above 0.99 for peak (III) and (IV).

Example 4

ATR-FTIR Detection of Polysorbate in Samples of Flu-CC Bulk

To demonstrate that the matrix did not impact the measurement of polysorbate, polysorbate 80 (in the amounts of 20 µg/ml, 50 µg/ml, 100 µg/ml, 250 µg/ml and 500 µg/ml) was added to samples of Flu-CC bulk. The samples contained azide as an internal standard, and were investigated using ATR-FTIR as described in Examples 2 and 3.

Figure 5:
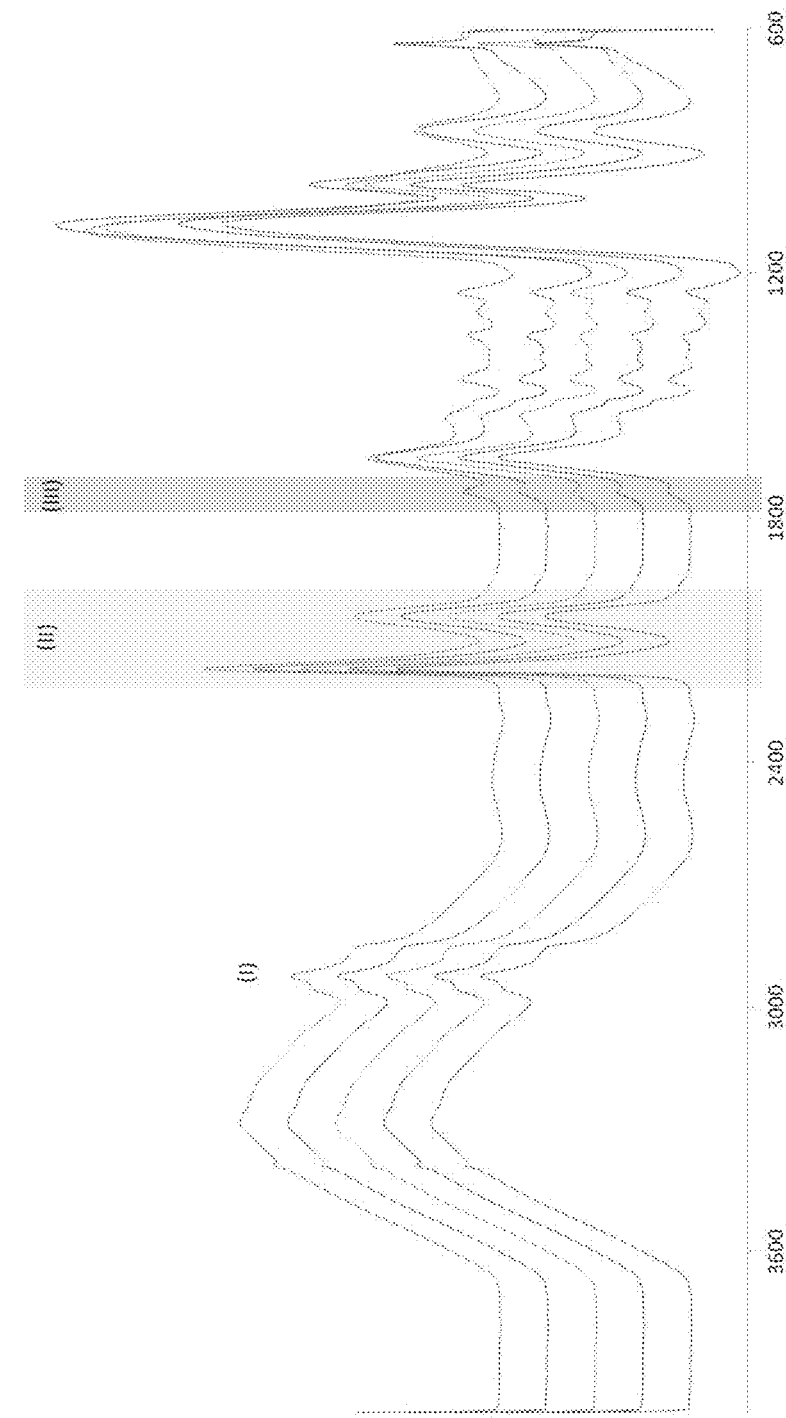
FIG. 5: Example of an ATR-FTIR spectra of a Flu-CC bulk sample, normalized using the internal standard (region II). Due to the complexity of the matrix, only peak (III) of FIG. 3 can be used to identify and quantify polysorbate 80 in Flu-CC samples.

FIG. 5 shows an example of spectra obtained from the polysorbate 80/Flu-CC samples. The five lines on FIG. 5 represent the five different polysorbate/flu samples, averaged from 32 scans, and normalized using the azide internal standard. (Peak areas (I), (II) and (III) are as reported in FIG. 3.)

The peak at 1735 cm$^{-1}$ (III) was identified as increasing accurately with added polysorbate 80 amounts. Due to the complexity of the matrix, only peak (III) can be used to identify and quantify polysorbate 80 in Flu-CC samples. See the linearity coefficients below.

Figure 6:
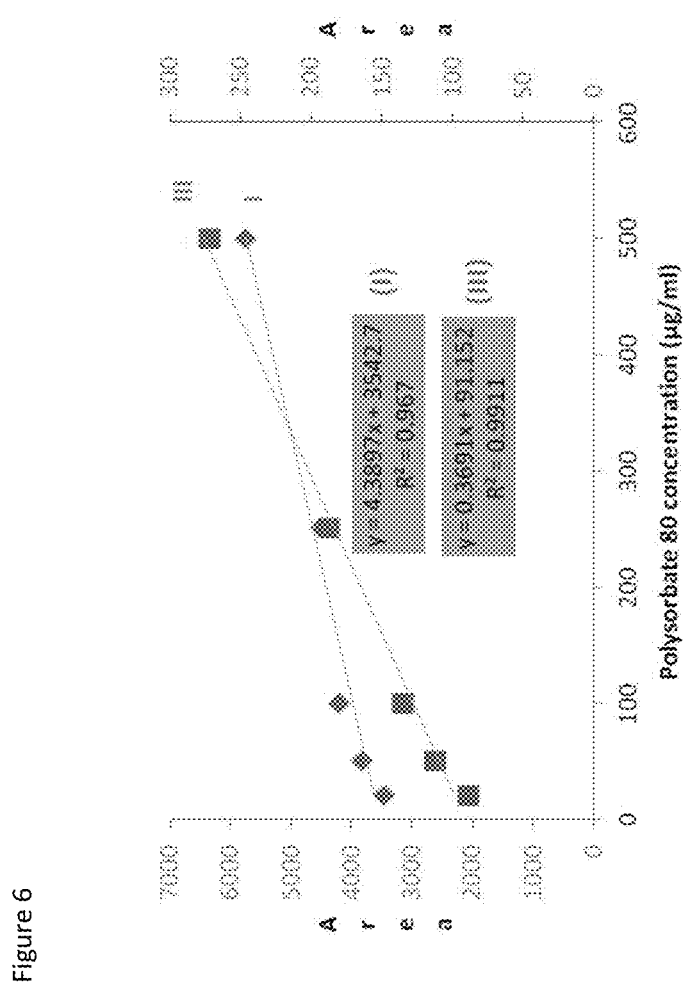
FIG. 6: graphs the area versus polysorbate 80 concentration from Region (I) and (III) of FIG. 5.

FIG. 6 shows the linear regression plotted for (I) and (III), using the five spectra of FIG. 5. The area is expressed as arbitrary units. The polysorbate 80 dose-response was shown to be linear in this range with coefficient of determination r$^2$ superior to 0.99 for peak (III). This indicates that the matrix did not significantly impact the measurement of polysorbate, and thus polysorbate in water can be used as a calibration curve.

Example 5

ATR-FTIR Detection of Polysorbate in Reference Standards and Influenza Samples

The data obtained in Examples 3 and 4 were used to calculate recovery values, as shown in Table 2. (Recovery value=% of known amount of polysorbate that was measured).

TABLE 2

| Sample | 20 µg/ml | 50 µg/ml | 100 µg/ml | 250 µg/ml | 500 µg/ml | Average |
|---|---|---|---|---|---|---|
| Polysorbate 80 in H$_2$O | 86% | 110% | 104% | 96% | 101% | 99% |
| Flu-CC bulk with added Polysorbate 80 | 80% | 89% | 88% | 90% | 98% | 89% |

Example 6

Use of Internal Standard

Figure 7A:
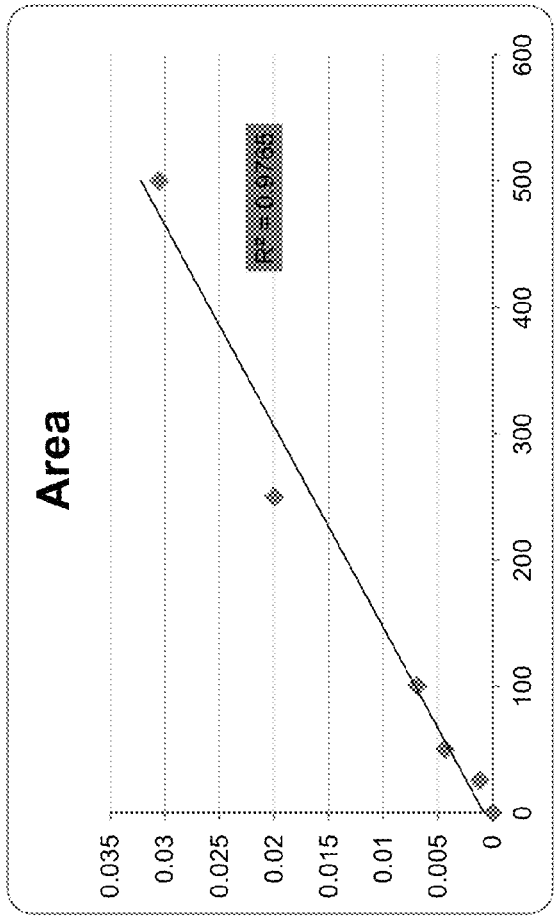
FIG. 7A: depicts polysorbate 80 spectra using ATR-FTIR.

FIGS. 7 and 8 depict the effect of using the internal standard in measuring polysorbate in bulk Flu-CC. FIG. 7A is a magnified view of an example of Peak III obtained using the ATR-FTIR method as described in Example 2, for three samples (results are average of 256 scans) without normalization. FIG. 8A is a magnified view of an example of Peak III obtained using the ATR-FTIR method as described in Example 2, for three samples (results are average of 256 scans) where the peaks have been normalized using the internal standard (peak area divided by area of internal standard peak).

Figure 7B:
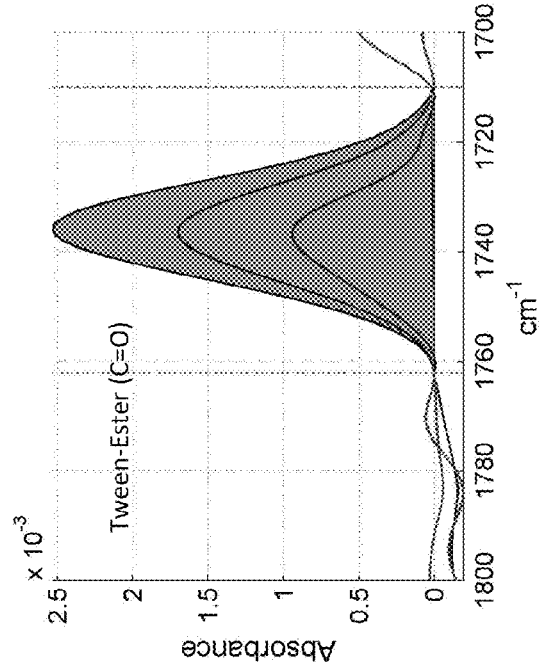
FIG. 7B: depicts quantification of polysorbate 80 using ATR-FTIR, where the peak response correlations are not normalized.

FIGS. 7B and 8B graph the peak areas vs. polysorbate concentration (X axis, µg/ml) for FIGS. 7 and 8, respectively. Normalization improves the linearity of the response (R$^2$=0.9933).

Example 7

Polysorbate Quantification in Samples of Flu-CC Bulk

Table 3: Polysorbate quantifications in Flu-CC bulk samples using GC-MS (method as described in Example 1) and ATR-FTIR (method as described in Example 2). All the samples are purified bulk or final bulk. The presence of polysorbate was due to the purification process utilized.

TABLE 3

| all antigens produced in cell culture | | | |
|---|---|---|---|
| Flu-CC Samples (Batch numbers) | GC-MS: polysorbate 80 concentration µg/ml | ATR-FTIR: polysorbate 80 concentration µg/ml | Ratio of GC-MS/ATR-FTIR measurements |
| DFCPB002 -Final | 216 | 249 | 0.87 |
| DFCPB003 -final | 124 | 175 | 0.71 |
| DFCPB004- final | 201 | 233 | 0.86 |
| DFCPBDA001 | 368 | 372 | 0.99 |
| DFCPBDA003 | 1124 | 1088 | 1.03 |
| DFCPBDA004 | 411 | 387 | 1.06 |
| DFCPBDA005 | 281 | 321 | 0.88 |
| DFCPBDA006 | 304 | 306 | 0.99 |
| EB66-61 Bulk A | 382 | 392 | 0.97 |
| EB66-61 Bulk B | 356 | 316 | 1.13 |
| EB66-69 Bulk A | 255 | 204 | 1.25 |
| EB66-69 Bulk B | 326 | 309 | 1.06 |
| EFCPAHA016-A | 268 | 294 | 0.91 |
| EFCPAHA026 | 122 | 128 | 0.95 |
| EFCPAHA028 | 129 | 191 | 0.68 |
| EFCPAHA037 | 338 | 351 | 0.96 |
| EFCPAHA038 | 737 | 789 | 0.93 |

The comparability of the results indicates that the ATR-FTIR method is a reliable alternative method for the quantification of polysorbate. The use of the present ATR-FTIR method for the quantification of polysorbate does not require chemical pretreatment of the sample, and does not show interference from purified bulk Flu-CC matrix.

Table 4 shows quantification of polysorbate 80 in samples obtained at different points during the processing of batch EB66-69 (cell culture). Good data correlation was observed between the two measurement methods.

TABLE 4

Polysorbate Quantification (GC-MS and ATR-FTIR)

| Process Steps EB66-69 | Sample buffer | Sample | Polysorbate 80 Measured conc. (GC-MS µg/ml) | Measured conc. (ATR-FTIR µg/ml) | Measured (µg/ml) |
|---|---|---|---|---|---|
| Ultrafiltration | PBS | UF1 | <51 | <LOQ | 0 |
| Ultracentrifugation | PBS-Tx100 | SN | 802 | 75 | 0 |
| Ultracentrifugation | PBS-Tx100 | SN | 858 | <LOQ | 0 |
| Detergent removal | PBS-Tw80-Tx100-VES | FT | <51 | 18* | 50-200 |
| Ultrafiltration | PBS-Tw80-Tx100-VES | UF2 | 520 | 539 | 100-500 |
| Sterilizing filtration | PBS-Tw80-Tx100-VES | Bulk | 255 | 219 | 100-500 |

*Noise
LOQ = limit of quantification

As shown in Table 4, the GC-MS technique indicated the presence of polysorbate prior to the addition of polysorbate 80.

Figure 9:
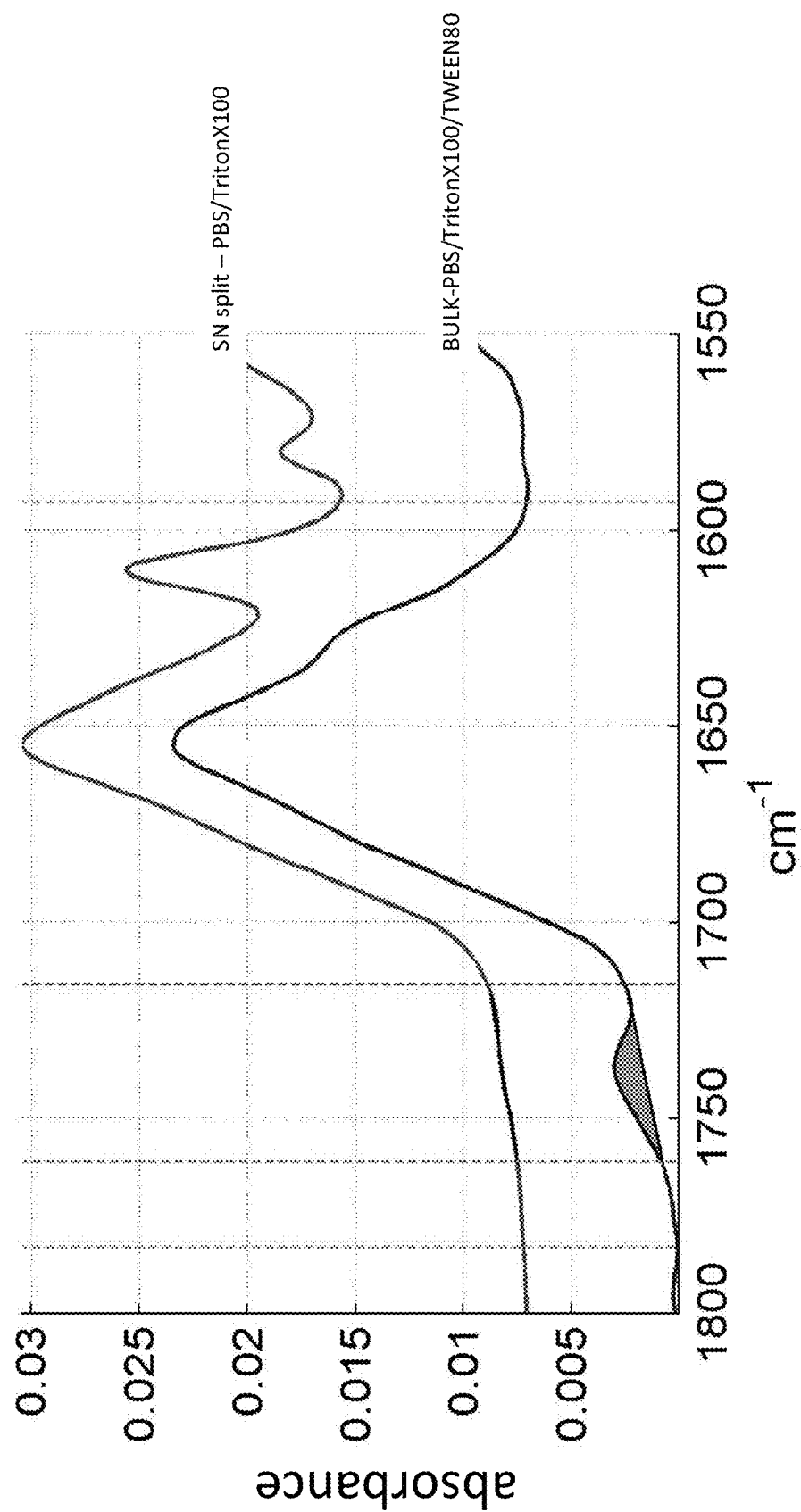
FIG. 9 depicts polysorbate 80 spectra from two samples obtained during purification of Flu-CC, where the top line is a sample taken prior to addition of polysorbate, and the bottom line is a sample taken after addition of polysorbate during processing.

FIG. 9 compares the ATR-FTIR measurement in the Peak III area, using samples from two different points in the process. The "SN split" sample was taken before any polysorbate was added during purification processing. FIG. 9 shows no interference in the Peak III area. Compare to "Bulk-PBS" sample, taken at a point in purification after polysorbate was added. This sample contains polysorbate (labeled as TWEEN80 on the graph). FIG. 9 demonstrates the specificity of the present ATR-FTIR technique for measuring polysorbate in a sample containing proteins.

ADDITIONAL REFERENCES

Baulsir and Simler, Design and evaluation of IR sensors for pharmaceutical testing, Advanced Drug Delivery Reviews 21(3): 191-203 (October 1996)

Blanco et al., Analytical control of pharmaceutical production steps by near infrared reflectance spectroscopy, Analytica Chimica Acta, 392(2-3):237 (1999)

Chang et al., Study of Interaction of Tributyl Phosphate, Non-ionic Surfactant and Water by FT-Infrared Spectrum. ISEC 2002, Cape Town, South Africa, 131-136, 2002

Hillgren et al., Protection mechanism of Tween 80 during freeze-thawing of a model protein, LDH, International Journal of Pharmaceutics 2002 237:1-2 (57-69)

Kato et al., Determination of polysorbates in foods by colorimetry with confirmation by infrared spectrophotometry, thin-layer chromatography, and gas chromatography, J Assoc Off Anal Chem. 1989 January-February; 72(1):27-9.

Kerwin et al., Effects of tween 80 and sucrose on acute short-term stability and long-term storage at −20° C. of a recombinant hemoglobin, Journal of Pharmaceutical Sciences 1998 87:9 (1062-1068)

Kishore et al., The degradation of polysorbates 20 and 80 and its potential impact on the stability of biotherapeutics. Pharm Res. 2011 May; 28(5):1194-210. Epub 2011 Mar. 3.

Li et al., Effect of poly(ethylene glycol) stearate on the phase behavior of monocaprate/Tween80/water system and characterization of poly(ethylene glycol) stearate-modified solid lipid nanoparticles, Colloids and Surfaces A: Physicochemical and Engineering Aspects 2008 317:1-3 (352-359)

Schwegman et al., Evidence of partial unfolding of proteins at the ice/freeze-concentrate interface by infrared microscopy, Journal of Pharmaceutical Sciences 2009 98:9 (3239-3246)

Tian et al., Enhanced brain targeting of temozolomide in polysorbate-80 coated polybutylcyanoacrylate nanoparticles, Int J Nanomedicine. 2011; 6:445-52. Epub 2011 Feb. 23.

Xie et al., Improvement of antifouling characteristics in a bioreactor of polypropylene microporous membrane by the adsorption of Tween 20, Journal of Environmental Sciences Volume 19, Issue 12, 2007, Pages 1461-1465

Xie et al., Surface modification of polyethylene membrane by adsorption of Tween 20 to improve antifouling characteristics in a bioreactor, Environmental Science and Technology, 2009

Xie et al., Surface modification of polypropylene microporous membranes by the adsorption of non-ionic surfactants, Chinese Journal of Polymer Science (English Edition) 24(4), July 2006, Pages 421-429

Yan and Chen, Investigation of microstructure of colloidal liquid aphrons (CLA), Journal of Xi'an Jiaotong University, 41(11):1351-54 (2007)

Yan and Chen, Zheng et al., FTIR study of Tween 80/1-butyl-3-methylimidazolium hexafluorophosphate/toluene microemulsions, Colloid Polymer Sci 287:871-876 (2009).

Yelenskii, et al., Phase state determination of tween-80-water binary mixtures by IR spectroscopy, Moscow University Chemistry Bulletin, 47 (6), pp. 386-392 (2006)

Zheng et al., FTIR study of Tween80/1-butyl-3-methylimidazolium hexafluorophosphate/toluene microemulsions, Colloid and Polymer Science 2009 287:7 (871-876)

What we claim is:

1. A method for determining the concentration of a polysorbate species in a mixture, comprising:
   a) obtaining a test sample of said mixture;
   b) adding an internal standard to said test sample;
   c) obtaining, with a spectrometer, a mid-infrared Attenuated Total Reflectance (ATR) spectra of the test sample;
   d) identifying, from the reflectance spectra, a wavenumber corresponding to the C=O peak;
   e) identifying, from the reflectance spectra, a wavenumber corresponding to the internal standard;
   f) calculating the area under the curve for said C=O wavenumber, normalized by the internal standard; and
   g) comparing said area to a calibration curve to determine the concentration of polysorbate in said test sample.

2. The method of claim 1 where said mixture comprises a protein antigen.

3. The method of claim 1 where said mixture comprises a protein antigen selected from the group consisting of influenza virus proteins; influenza hemagglutinin (HA) proteins; influenza neuraminidase (NA) proteins; measles virus proteins, mumps virus proteins, varicella virus (chickenpox) proteins, rubella virus proteins, dengue virus proteins, Respiratory Syncytial Virus (RSV) proteins, Cytomegalovirus (CMV) proteins, Human Papillomavirus (HPV) proteins; hepatitis A virus proteins; hepatitis B virus proteins; rotavirus proteins; poliovirus proteins; measles virus proteins; herpes virus proteins; smallpox virus proteins; poxvirus proteins; *S. pneumococcus* proteins; *Haemophilus influenzae* B proteins; *Corynebacterium diphtheria* proteins; *Corynebacterium* species proteins; *Clostridium tetani* proteins; *Clostridium* species proteins; *Bordetella pertussis* proteins; and *Bordetella* species proteins.

4. The method of claim 1 where said mixture comprises a polysaccharide antigen.

5. The method of claim 1 where said mixture comprises a polysaccharide antigen selected from the group consisting of *Streptococcus* species polysaccharides; *Streptococcus pneumonia* polysaccharides, *Neisseria meningitides* polysaccharides; *Haemophilus influenza* polysaccharides; *Salmonella* species polysaccharides; and *Salmonella typhi* polysaccharides.

6. The method of claim 1, where said test sample is not chemically pretreated prior to obtaining the mid-infrared attenuated total reflectance spectra of the test sample.

7. The method of claim 1, wherein the wavenumber corresponding to the C=O peak is approximately 1735 $cm^{-1}$.

8. The method of claim 1, where said internal standard is azide.

9. The method of claim 1, where said test sample is an aqueous sample.

10. The method of claim 1, where said mixture comprises only a single polysorbate species.

11. The method of claim 1, where said mixture comprises a polysorbate species selected from polysorbate 80, polysorbate 60, polysorbate 40 and polysorbate 20.

12. The method of claim 1, where said mixture comprises polysorbate 80.

13. The method of claim 1 where said mixture comprises a non-polysorbate excipient selected from 4-(1,1,3,3-Tetramethylbutyl)phenyl-polyethylene glycol, t-Octylphenoxypolyethoxyethanol, Polyethylene glycol tert-octylphenyl ether and Vitamin E succinate (VES).

14. The method of claim 1 where said mixture is a bulk vaccine component.

15. The method of claim 1 where said mixture is a bulk influenzae vaccine component.

16. The method of claim 1, where said test sample is placed in contact with a single Internal Reflectance Element (IRE) prior to obtaining the ATR specta.

17. The method of claim 1, where said test sample is placed in contact with a multiple Internal Reflectance Element (IRE) prior to obtaining the ATR specta.

18. The method of claim 1 where said test sample is placed on a IRE made of diamond prior to obtaining the ATR specta.

19. The method of claim 1 where the sample is dried under nitrogen prior to obtaining the spectra.

20. A method according to claim 1 where said mixture is an aqueous solution comprising a single polysorbate species, and where said method comprises adding azide to said test sample as an internal standard; measuring the peak area at 1735 $cm^{-1}$ and at 2200-1980 $cm^{-1}$ using ATR-FTIR; normalizing said peak area at 1735 $cm^{-1}$ with said peak area at 2200-1980 $cm^{-1}$, and determining the normalized peak area at 1735 $cm^{-1}$.

* * * * *